United States Patent [19]

Kanamaru et al.

[11] Patent Number: 4,987,144
[45] Date of Patent: Jan. 22, 1991

[54] 1,3-BIS(1,2,4-TRIAZOL-1-YL)2-(4-TRI-FLUOROMETHYLPHENYL)PROPAN-2-OL USEFUL FOR THE PREVENTION AND/OR TREATMENT OF DEEP-SEATED MYCOSIS

[75] Inventors: Yoshihiko Kanamaru; Minoru Tokizawa, both of Narita; Masaru Matsumoto, Tomisato; Takemitsu Asaoka, Narita; Hideaki Matsuda, Abiko; Tadayuki Kuraishi, Chiba, all of Japan

[73] Assignee: SS Pharmaceutical Co., Ltd., Tokyo, Japan

[21] Appl. No.: 412,152

[22] Filed: Sep. 25, 1989

[30] Foreign Application Priority Data

May 2, 1989 [JP] Japan ................... 64-113113

[51] Int. Cl.$^5$ .................... A61K 31/41; C07D 249/08
[52] U.S. Cl. ................... 514/383; 548/266.6
[58] Field of Search ................ 548/266.6; 514/383

[56] References Cited

U.S. PATENT DOCUMENTS 4,416,682  11/1983  Worthington ............. 548/266.2

OTHER PUBLICATIONS

Boyle, "Antifungal Triazole Compound", CA 103:141980b (1985).

Primary Examiner—Glennon H. Hollrah
Assistant Examiner—Patricia L. Morris
Attorney, Agent, or Firm—Oblon, Spivak, McClelland, Maier & Neustadt

[57] ABSTRACT

Disclosed herein is 1,3-bis(1,2,4-triazol-1-yl)-2-(4-trifluoromethylphenyl)propan-2-ol represented by the following formula (I):

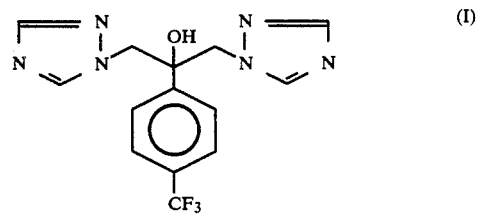

An antimycotic preparation containing the triazole compound (I) is also disclosed. Also disclosed is a method for the prevention and/treatment of a deep-seated mycosis of a human or mammal, which comprises administering an effective dose of the triazole compound (I) to the human or mammal.

3 Claims, No Drawings

1,3-BIS(1,2,4-TRIAZOL-1-YL)2-(4-TRIFLUOROME-THYLPHENYL)PROPAN-2-OL USEFUL FOR THE PREVENTION AND/OR TREATMENT OF DEEP-SEATED MYCOSIS

BACKGROUND OF THE INVENTION (1) Field of the Invention

This invention relates to a novel triazole compound having excellent antimycotic activities and high safety in combination, an antimycotic preparation containing same as an active ingredient, and a method for the prevention and/or treatment of a deep-seated mycosis by using same.

(2) Description of the Related Art

Mycoses include skin diseases represented by various trichophytoses, eczema marginatum, psoriases and cutaneous candidiases as well as deep-seated mycoses typified by fungal meningitis, fungal infectious inspirator disease, fungemia and urinary tract mycosis.

Of these, deep-seated mycoses cannot be treated with conventional antibiotics or chemotherapeutic agents. There is an observable tendency to increased patients suffering from these diseases. There has accordingly a strong desire for the development of a drug effective for the treatment of these diseases.

Only a few therapeutic agents have heretofore been sued, including polyene antibiotics such as nystatin and amphotericin B, azole compounds such as miconazole, and pyrimidine compounds such as flucytosine.

These drugs are however not fully satisfactory, because they are accompanied by the problem that installation is only feasible for administration due to toxicity or the like or even if oral administration is possible problems arise in the kidneys, bone marrow, stomach and/or the like or the antimycotic spectrum is narrow.

Ketoconazole, fluconazole and the like have been studied and developed recently as azole drugs for the treatment of deepseated mycoses. However, these azole compounds include very few compounds which can exhibit antimycotic activities when administered by a simple method such as oral administration. Under the circumstances, it is not believed to be too much to say that it is only fluconazole that has potential utility as a medicine in practice. Fluconazole is disclosed in U.S. Pat. No. 4,404,216.

However, fluconazole is not free of side effects and can hardly be regarded satisfactory from the standpoint of safety.

There was hence been a desire for the development of a compound having antimycotic activities equal to or higher than fluconazole and moreover having higher safety than fluconazole upon administration.

SUMMARY OF THE INVENTION

Under the above-described circumstances, the present inventors have synthesized numerous compounds and have also conducted an investigation on their pharmacological effects. As a result, it has now been found that the triazole compound represented by the formula (I) set out below has excellent specific antimycotic activities and a high level of safety and is extremely useful as an antimycotic agent.

In one aspect of this invention, there is thus provided 1,3bis-(1,2,4-triazole-l-yl)-2-(4-trifluoromethylphenyl)-propan-2-ol represented by the following formula (I):

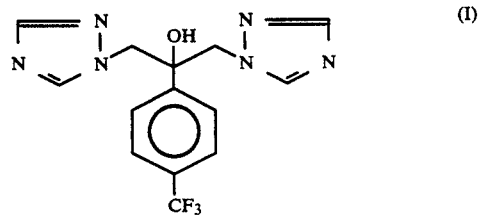

In another aspect of this invention, there is also provided an antimycotic preparation comprising as an active ingredient the triazole compound (I).

In a further aspect of this invention, there is also provided a method for the prevention and/treatment of a deep-seated mycosis of a human or mammal, which comprises administering an effective dose of the triazole compound (I) to the human or mammal.

The triazole compound (I) according to this invention exhibits more specific antimycotic activities compared to similar compounds as will be readily understood from a referential test which will be described herein. As will also be demonstrated in the same referential test, its apothanasia effects upon oral administration are greater than fulconazole whose development as an oral preparation is now under way. Furthermore, body weight reductions were observed after administration in a group administered with fluconazole, thus indicating the existence of side effects. In contrast, the body weight increased steadily in a group administered with the triazole compound (I) of this invention. It is therefore evident that the triazole compound (I) of this invention is far superior in safety to fluconazole.

In addition, the acute toxicity of the triazole compound (I) according to this invention is 1,200 mg/kg in terms of $LD_{50}$ (mice; P.O.). It is therefore possible to effectively and safely treat and/or prevent a deep-seated mycosis of human or a mammal such as a dog, cat, horse, cow, pig, sheep or monkey, said deep-seated mycosis being induced by infection or by a fungus existing in the body, by oral administration of the compound.

DESCRIPTION OF THE INVENTION AND PREFERRED EMBODIMENTS

Some compounds similar to 1,3-bis(1,2,4-triazol-l-yl)-2-(4-trifluoromethylphenyl)propan-2-ol (hereinafter abbreviated as the "triazole compound") of this invention have already been disclosed in U.S. Pat. No. 4,416,682. However, the triazole compound of this invention is not specifically disclosed in the above prior art publication and is hence novel.

The triazole compound of this invention can be easily synthesized by any one of the processes disclosed in the prior art publication, for example, by the process represented by the following equation:

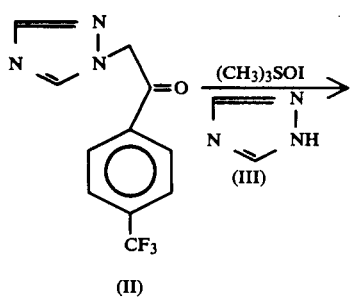

(II)

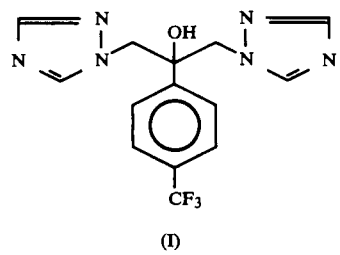

(I)

Namely, the triazole compound (I) can be prepared by reacting 2-(1,2,4-triazol-1-yl)-4'-trifluoromethylacetophenone (II) and 1,2,4-triazole (III) at room temperature or under reflux conditions, for one to several tens hours, in the presence of trimethylsulfoxonium iodide and an alkali, in an alcohol such as t-butanol.

The target triazole compound (I) can be obtained in a substantially pure form by distilling out the solvent from the reaction mixture after completion of the reaction, adding water to the residue, extracting the resultant mixture with a solvent such as ethyl acetate, washing the extract thus obtained and then distilling out the solvent. The resultant compound may then be subjected to purification such as column chromatography or recrystallization as needed, thus obtaining the target compound in a purified form.

If necessary, the triazole compound obtained as described above can be converted into a salt such as the hydrochloride, nitrate, hydrobromide, sulfate, p-toluenesulfonate, methanesulfonate, fumarate, maleate, succinate or lactate.

When the triazole compound of this invention is orally administered as an antimycotic agent, the dose varies depending on the patient's weight, age, sex and conditions, the preparation form, etc. In general, it is however suitable to administer about 5–1,000 mg of the triazole compound in the case of oral administration and about 1–500 mg of the triazole compound in the case of parenteral administration, both per day and per human adult, in 1–4 portions.

It is preferable to administer the antimycotic agent of this invention orally in the form of tablets, granules, powder, capsules or suspension prepared in a manner known per se in the art. However, it can also be administered parenterally in the form of an injection. To produce a solid preparation for oral administration, the triazole compound (I) is added with an excipient and optionally with a binder, a disintegrator, a lubricant, a colorant, a corrigent, an extender, a coating agent, a sugar coating material and/or the like, followed by formation into tablets, granules, powder, capsules or the like by a method known per se in the art. To prepare an injection on the other hand, the triazole compound (I) is optionally dissolved in an oil such as olive oil or sesame oil and is then formulated into a subcutaneous or intramuscular injection. As an alternative, a surfactant or the like is added to formulate a so-called solubilized preparation.

The present invention will hereinafter be described in further detail by the following examples, tests and preparation example. It should however be borne in mind that the present invention is not limited to or by them.

EXAMPLE

In 10 mλ of t-butanol were dissolved 1.02 g of 2-(1,2,4-triazol-1-yl)-4'-trifluoromethylacetophenone, 2.28 g of trimethylsulfoxonium iodide, 1.20 g of potassium hydroxide and 0.33 g of 1,2,4-triazole. The resultant mixture was stirred at 70° C. for 16 hours. After completion of the reaction, the solvent was distilled out, water was added to the residue, and the resulting mixture was extracted with ethyl acetate. The organic layer was washed with water and then dried over anhydrous magnesium sulfate. The solvent was thereafter distilled out. Using chloroform, the residue was purified by chromatography on a silica gel column to obtain 0.69 g of the triazole compound (I) as colorless crystals (yield: 51%).

Melting point: 170–172° C. IR (KBr), cm$^{-1}$: 3230, 1620, 1507, 1320.

NMR (δ ppm in CDCl$_3$): 4.55 (4H,s), 7.20–7.85 (4H, m), 7.92 (2H,s), 8.02 (2H,s).

TEST 1

Antimycotic activities

Male ICR mice of 4 weeks old were used as groups, each consisted of 5 mice. Each mouse was inoculated at caudal vein with $2.8 \times 10^6$ cells of *Candida albicans*. From one hour after the inoculation, each test compound was dissolved in 0.5 mλ of 0.06 N hydrochloric acid which had been added with "0.2% TO−10M" (trade name; product of Nikko Chemicals Co., Ltd.) and was orally administered once a day, four times in total. The mice were observed until the 14th day after the inoculation of the fungus. The average survival days of each group was compared with those of the control group to determine T/C (%). The results are summarized in Table 1.

$$T/C\ (\%) = \frac{\text{Average survival days of group administered with test compound}}{\text{Average survival days of control group}}$$

TABLE 1

| Test compound | Dose (mg/kg) | T/C (%) |
|---|---|---|
| Triazole compound (I) | 5 | 450 |
|  | 2.5 | 385 |
|  | 1.25 | 186 |
| Fluconazole (control drug) | 5 | 443 |
|  | 2.5 | 379 |
|  | 1.25 | 143 |
| Control | — | 100 |

REFERENTIAL TEST

Antimycotic activities

In a manner similar to Test 1, antimycotic activities of each of the test compounds shown below in Table 2 were investigated. As will be readily envisaged from the results, practically no antimycotic activities were observed from the oral administration of those compounds.

Test compounds:

(A) Structure: bis-triazole with central C(OH)(R), R substituent varies

| R in formula (A) | Dose (mg) | T/C |
|---|---|---|
| 4-CN, 3-F phenyl | 40 | 81 |
| 4-(4-F-phenyl)phenyl | 40 | 136 |
| 3-F, 4-NHCOCH₃ phenyl | 40 | 82 |
| 3,5-bis(CF₃) phenyl | 20 | 118 |
| 3-OC₃H₇, 4-F phenyl | 40 | 125 |
| 2,6-diF, 3-OH phenyl | 40 | 82 |
| 2,6-diF, 3-OCH₃ phenyl | 40 | 91 |
| 2,6-diF, 3-OCH₂C₆H₅ phenyl | 40 | 73 |

-continued

Test compounds: (A)

| R in formula (A) | Dose (mg) | T/C |
|---|---|---|
| 2-F, 6-(OCH₂-phenyl) phenyl | 40 | 122 |
| 2,4-diF, 6-(OCH₂-phenyl) phenyl | 40 | 117 |
| 3,4-diF, 6-OH phenyl | 40 | 125 |

TEST 2

Measurement of body weight variations

With respect to the laboratory animals administered with 2.5 mg/Kg of the respective test compounds in Test 1, body weight variations were investigated along the passage of time. The results are summarized in Table 2.

TABLE 2

| Days after administration | Triazole compound (I) | Fluconazole |
|---|---|---|
| 0 | 21.0 g | 21.0 g |
| 1 | 20.6 | 20.2 |
| 2 | 21.4 | 20.6 |
| 3 | 22.2 | 20.4 |
| 4 | 23.0 | 20.8 |
| 5 | 23.3 | 20.4 |
| 6 | 23.1 | 19.4 |

PREPARATION EXAMPLE 1

| Tablets | |
|---|---|
| Triazole compound (I) | 50 mg |
| Crystalline cellulose | 50 mg |
| Lactose | 50 mg |
| Hydroxypropylcellulose | 18 mg |
| Magnesium stearate | 2 mg |
| TOTAL | 170 mg |

Tablets of the above composition were produced by a method known per se in the art. It is possible to treat those tablets into sugar coated tablets or film coated tablets as needed.

PREPARATION EXAMPLE 2

| Capsules | |
| --- | --- |
| Triazole compound (I) | 50 mg |
| Light anhydrous silicic acid | 25 mg |
| Lactose | 100 mg |
| Starch | 50 mg |
| Talc | 25 mg |
| TOTAL | 250 mg |

The above mixture was filled in No. 1 capsules to obtain capsules.

PREPARATION EXAMPLE 3

| Granules | |
| --- | --- |
| Triazole compound (I) | 50 mg |
| Lactose | 600 mg |
| Corn starch | 200 mg |
| Sodium carboxymethylcellulose | 20 mg |
| Hydroxypropylcellulose | 130 mg |
| TOTAL | 1,000 mg |

Granules of the above composition were produced by a method known per se in the art.

PREPARATION EXAMPLE 4

| Powder | |
| --- | --- |
| Triazole compound (I) | 50 mg |
| Light anhydrous silicic acid | 20 mg |
| Precipitated calcium carbonate | 10 mg |
| Lactose | 250 mg |
| Starch | 70 mg |
| TOTAL | 400 mg |

Powder of the above composition was produced by a method known per se in the art.

PREPARATION EXAMPLE 5

| Injection | |
| --- | --- |
| Triazole compound (I) | 5 mg |
| Hydrogenated castor oil | 85 mg |
| Propylene glycol | 60 mg |
| Glucose | 50 mg |
| Distilled water for injection | to total volume of 1 ml |

Injection of the above composition was produced by a method known per se in the art.

PREPARATION EXAMPLE 6

| Injection | |
| --- | --- |
| Triazole compound (I) | 5 mg |
| Polyoxyethylene-hydrogenated castor oil | 40 mg |
| Propylene glycol | 60 mg |
| Distilled water for injection | to total volume of 1 ml |

Injection of the above composition was produced by a method known per se in the art.

We claim:

1. 1,3-Bis(1,2,4-triazol-1-yl)-2-(4-trifluoromethylphenyl)propan-2-ol represented by the following formula (I):

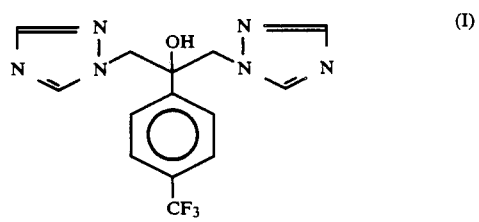

2. A pharmaceutical antimycotic preparation which comprises an effective amount of a compound of the following formula (I):

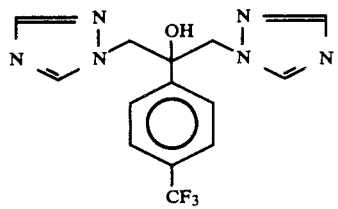

together with a pharmaceutically acceptable diluent or carrier.

3. A method for the prevention and/or treatment of a deep-seated mycosis of a human or mammal, which comprises administering to the human or mammal an effective does of 1,3-bis (1,2,4-trizol-l-yl)-2-(4-trifluoromethylphenyl) propan-2-ol represented by the following formula (I):

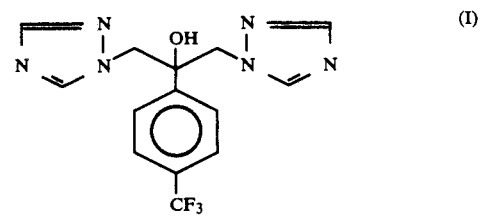

* * * * *